United States Patent [19]
Yokozuka

[11] Patent Number: 4,942,879
[45] Date of Patent: Jul. 24, 1990

[54] MERCURY SPHYGMOMANOMETER
[75] Inventor: Tsuchiyasu Yokozuka, Fujioka, Japan
[73] Assignee: Yamasu Co., Ltd., Saitama, Japan
[21] Appl. No.: 293,408
[22] Filed: Jan. 4, 1989
[30] Foreign Application Priority Data
  Mar. 22, 1988 [JP] Japan .................... 63-65696
[51] Int. Cl.⁵ ............................. A61B 5/023
[52] U.S. Cl. .................... 128/684; 128/685
[58] Field of Search ............ 128/672, 677–686; 73/747–748

[56] References Cited
U.S. PATENT DOCUMENTS
1,830,829 11/1931 Eyster ................. 73/748 X
4,090,503 5/1978 Speidel ............... 128/684

FOREIGN PATENT DOCUMENTS
1002456 6/1952 France ............... 128/684

Primary Examiner—Angela D. Sykes
Attorney, Agent, or Firm—Armstrong, Nikaido, Marmelstein, Kubovcik & Murray

[57] ABSTRACT

A mercury sphygmomanometer has an air pump connected to the top of a mercury passage through a tube so that the pump is activated in response to an operation of closing a cover. Accordingly, it is possible to return the mercury left in the mercury passage to the mercury reservoir by means of the air pump which is activated in response to a cover closing operation and close the valve after the mercury has been expelled from the mercury passage to thereby cut off the communication between the mercury passage and the mercury reservoir.

3 Claims, 3 Drawing Sheets

TO CUFF 6

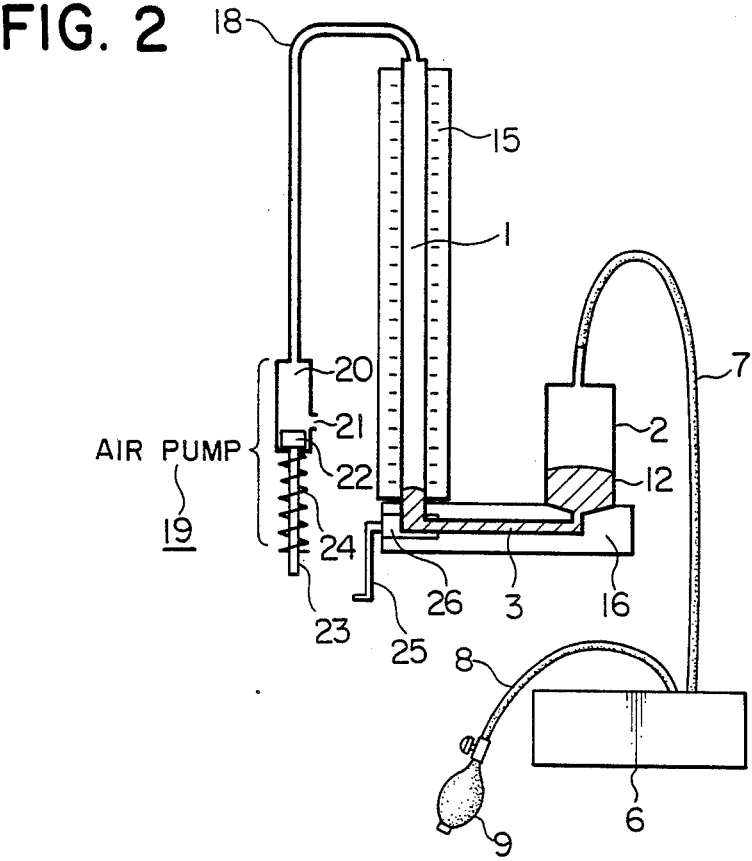
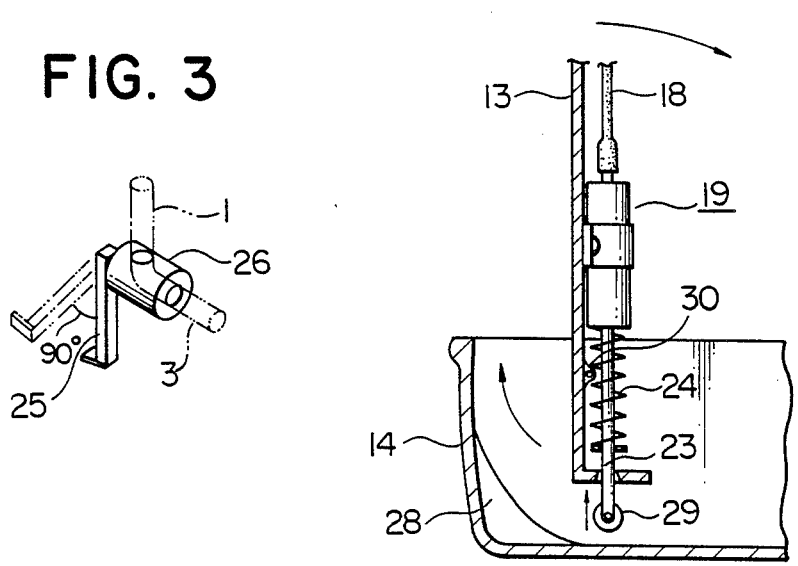

MERCURY SPHYGMOMANOMETER

BACKGROUND OF THE INVENTION

The present invention relates to a mercury sphygmomanometer. More particularly, the present invention pertains to a mercury sphygmomanometer which is capable of being housed in a casing.

FIG. 6 is a partially-sectioned schematic view showing a conventional mercury sphygmomanometer.

Referring to FIG. 6, a mercury passage 1 is connected to a mercury reservoir 2 through a communicating tube 3. The tube 3 is provided with a cock 4 which is opened and closed by means of a handle 5.

A cuff, or wrapping sleeve, 6 is connected to the mercury reservoir 2 through a tube 7 and also connected to a bulb 9 through a tube 8. The mercury passage 1 is provided at its upper end with a filter 10 and a small bore 11 through which the mercury passage 1 is communicated with the outside air. The reference numeral 12 denotes mercury.

In actual use, the cuff 6 is wrapped around the arm and, with the cock 4 opened, air is pumped into the cuff 6 by means of the bulb 9. In consequence, the mercury 12 in the mercury reservoir 2 rises through the mercury passage 1, thus enabling measurement of blood pressure.

After use, the mercury passage 1 is tilted to return all the mercury remaining in the passage 1 to the mercury reservoir 2 and then the cock 4 is closed in order to prevent leakage and contamination of the mercury 12.

There is another type of conventional mercury sphygmomanometer having an arrangement in which a cover is formed together with the mercury passage in one unit so that, as the cover is closed, the cock is automatically closed.

Of the above-described conventional apparatuses, the former, that is, the prior art wherein mercury is returned by tilting the mercury passage, has the disadvantage that the cock must be opened and closed every time the apparatus is used. Further, if the sphygmomanometer is moved with the cock left opened because the operator forgot to close it, a contaminative substance in the mercury reservoir may enter the mercury passage and adhere to the wall thereof, resulting in the mercury passage being stained.

There is also a fear of the mercury column becoming discontinuous; in such a case, air enters the space between the separated portions of the mercury column, thus causing adverse effects on the measuring accuracy. To remove the air, the mercury passage must be tapped or swung.

The latter, that is, the prior art wherein the cock is automatically opened and closed in response to an operation of opening and closing the cover, has the disadvantage that mercury is not completely returned to the mercury reservoir when the cover is closed.

SUMMARY OF THE INVENTION

In view of the above-described circumstances, it is a primary object of the present invention to provide a mercury sphygmomanometer which is designed so that the mercury which is left in the mercury passage is completely returned to the mercury reservoir in response to an operation of closing the cover.

To this end, according to the present invention, an air pump is connected to the top of the mercury passage through a tube so that the pump is activated in response to an operation of closing the cover.

Accordingly, it is possible to return the mercury left in the mercury passage to the mercury reservoir by means of the air pump which is activated in response to a cover closing operation and close the valve after the mercury has been expelled from the mercury passage to thereby cut off the communication between the mercury passage and the mercury reservoir.

BRIEF DESCRIPTION OF THE DRAWINGS

FIG. 2 shows the connection relationship between the elements that constitute in combination the arrangement shown in FIG. 1 in terms of the passage of air;

FIG. 3 is a fragmentary perspective view showing the arrangement and operation of the valve employed in the embodiment;

FIG. 4 is a fragmentary view showing the way in which the air pump employed in the embodiment operates;

DESCRIPTION OF THE PREFERRED EMBODIMENTS

Embodiments of the present invention will be described herein with reference to the accompanying drawings.

Figure 1:
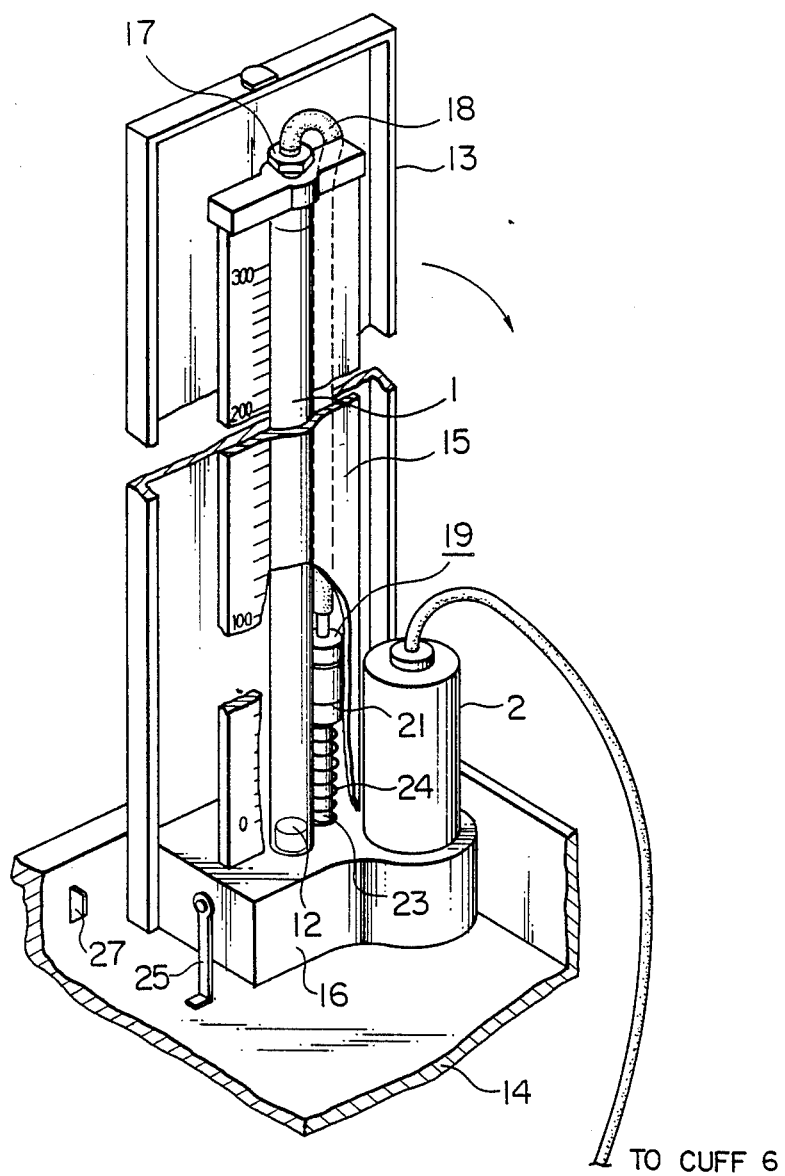
FIG. 1 is a perspective view showing the general arrangement of one embodiment of the mercury sphygmomanometer according to the present invention.

FIG. 1 is a perspective view showing the general arrangement of one embodiment of the mercury sphygmomanometer according to the present invention, while FIG. 2 shows the connection relationship between the elements that constitute in combination the arrangement shown in FIG. 1 in terms of the passage of air.

Figure 6:
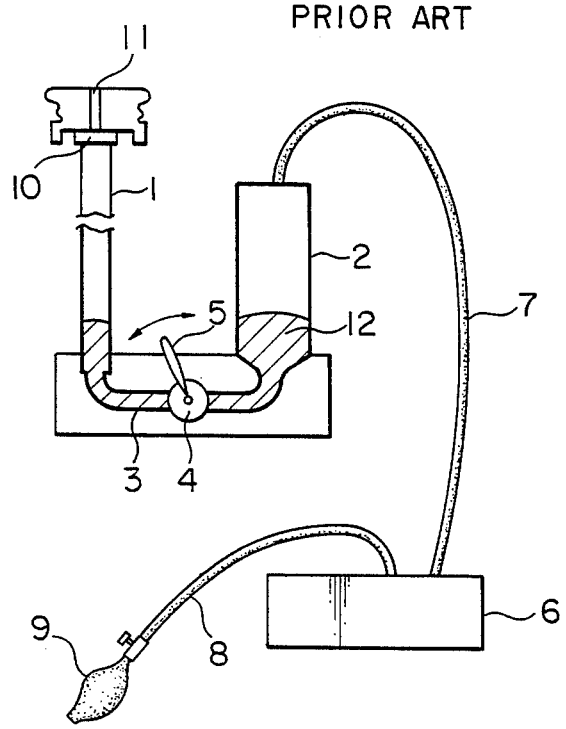
FIG. 6 is a partially-sectioned schematic view showing a conventional mercury sphygmomanometer.

In FIGS. 1 and 2, the same elements as those shown in FIG. 6 are denoted by the same reference numerals. A cover 13 is pivotally attached to a casing 14 so that the cover 13 is capable of pivoting in the direction of the solid-line arrow to close the casing 14. A mercury passage 1 is disposed in the center of the cover 13. A calibration plate 15 is attached in such a manner as to support the mercury passage 1. A base 16 is provided at the lower end of the cover 13. The mercury passage 1 and a mercury reservoir 2, which are mounted on the upper side of the base 16, are connected to each other through a communicating tube 3 inside the base 16 (see FIG. 2).

The top of the mercury passage 1 is connected to a tube 18 through a connecting member 17, and the distal end of the tube 18 is connected to an air pump 19.

The air pump 19 includes a cylinder 20 and a bore 21 which is provided in the side wall of the cylinder 20. A piston 22 is received in the cylinder 20, and a rod 23 projects from one end of the cylinder 20. It should be noted that the reference numeral 24 denotes a spring.

The reference numeral 25 denotes a lever which is actuated to open and close a valve 26. A projection 27 is provided on one end of the casing 14 such that the projection 27 abuts against the lever 25 and causes it to pivot (described later).

FIG. 3 is a fragmentary perspective view showing the arrangement and operation of the valve 26 which is provided inside the base 16.

When the apparatus is in the state shown in FIG. 1, the lever 25 extends vertically as shown by the solid line; at this time, the valve 26 is open to provide communication between the communicating tube 3 and the mercury passage 1. When the lever 25 is tilted at an angle of 90° as shown by the chain line, the valve 26 cuts off the communication between the communicating tube 3 and the mercury passage 1.

FIG. 4 is a fragmentary view showing the way the air pump 19 operates, in which illustration of the other constituent elements is omitted.

In the figure, the reference numeral 28 denotes a slope which is arranged such that, when the cover 13 is closed in the direction of the illustrated arrow, the slope 28 comes into contact with a roller 29 attached to the distal end of the rod 23 and causes the rod 23 to be pushed up.

It should be noted that the reference numeral 30 denotes a point at which the cover 13 is pivotally attached to the casing 14; therefore, the cover 13 pivots about the point 30.

The operation of the above-described embodiment will next be explained.

First, when the cover 13 is in its open position, that is, when the apparatus is in an operative state, the lever 25 is placed in the vertical position (shown by the solid line in FIG. 3) by means of the biasing force from a spring (not shown) to open the valve 26. Therefore, the mercury passage 1 and the mercury reservoir 2 are in communication with each other.

At this time, the rod 23 of the air pump 19 is fully expanded by means of the spring 24 (see FIG. 4) and the piston 22 is disposed at the lowermost position inside the cylinder 20, as clearly shown in FIG. 2.

Accordingly, the bore 21 which is provided in the side wall of the cylinder 20 is open and the inside of the cylinder 20 is in communication with the outside air.

In short, when the cover 13 is open, there is no obstruction to the flow of air within the mercury passage 1 when the mercury column in the passage 1 rises and falls, thus enabling measurement of blood pressure.

After the use of the apparatus, the cover 13 is closed in the direction of the solid arrow. As the cover 13 is moved in the closing direction about the pivot point 30 (see FIG. 4), the roller 29 comes into contact with the slope 28 and pushes up the rod 23 against the force from the spring 24. As the rod 23 is pushed up, the piston 22 performs a pumping action while closing the bore 21, thus pumping the air contained in the cylinder 20 into the mercury passage 1 through the tube 18.

As a result, the mercury 12 which is left in the mercury passage 1 is returned to the mercury reservoir 2 via the communicating tube 3. When the mercury 12 is being forced back to the mercury reservoir 2, the lever 25 comes into contact with the projection 27 and is thereby tilted at an angle of 90° (shown by the chain line in FIG. 3) to close the valve 26.

Accordingly, when the cover 13 is closed, the mercury 12 left in the mercury passage 1 is pushed back to the mercury reservoir 2 and the valve 26 is also closed.

The operation that is conducted in the process of opening the cover 13 is completely reverse to that in the process of closing the cover 13; therefore, description thereof is omitted.

Since the position of the piston 22 with respect to the angle at which the cover 13 is closed is constant independently of the speed at which the cover 13 is closed, the way in which the mercury 12 is returned is also constant and there is therefore no fear of the mercury 12 remaining in the mercury passage 1 even if the cover 13 is closed quickly.

It should be noted that the valve closing timing is set so that the valve 26 is closed when all the remaining mercury 12 has moved toward the mercury reservoir 2 beyond the valve 26.

According to this embodiment, when the cover 13 is fully closed, the mercury 12 is automatically forced back to the mercury reservoir 2 and the valve 26 is also automatically closed.

Figure 5:
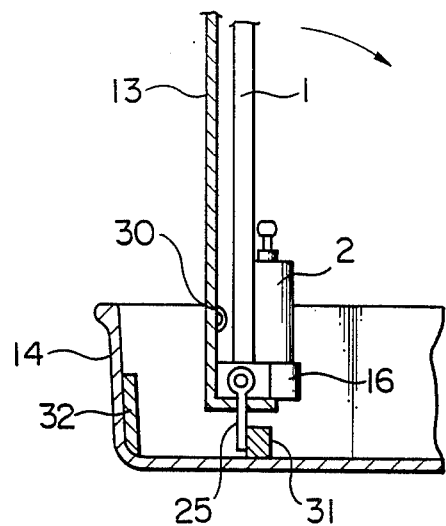
FIG. 5 is a fragmentary view schematically showing the arrangement of another embodiment of the mercury sphygmomanometer according to the present invention.

FIG. 5 is a fragmentary schematic view of another embodiment of the present invention, which shows only constituent elements which are related to the mercury column in a state wherein the cover 13 is in its open position.

This embodiment differs from the above-described embodiment only in the arrangement of a lever actuating mechanism. In FIG. 5, the same reference numerals as those shown in FIGS. 1 to 4 denote the same elements.

In the figure, the reference numerals 31 and 32 denote lever abutments. When the cover 13 is opened, the lever 25 comes into contact with the abutment 31 to open the valve 26 (shown in the already-described embodiment).

On the other hand, when the cover 13 is closed to a predetermined angle, the lever 25 comes into contact with the abutment 32 to start to close the valve 26. When the cover 13 is fully closed, the lever 25 is rotated 90° from the "open" position to completely shut off the mercury passage 1.

Since the arrangements of the other portions are the same as in the first-described embodiment, the mercury 12 has previously been forced back to the mercury reservoir 2 by means of the air pump 19; therefore, when the valve 26 is closed, no mercury is present in the mercury passage 1.

In this embodiment also, when the cover 13 is closed, the mercury 12 is automatically pushed back to the mercury reservoir 2 and the valve 26 is also automatically closed.

As has been described above, according to the present invention, the mercury which is left in the mercury passage is forced back to the mercury reservoir by means of the air pump before the cover is fully closed, and the passage of mercury is closed after the mercury has been expelled from the mercury passage. Therefore, it is possible to provide a mercury sphygmomanometer which is not only free from contamination of the mercury but also improved in its measuring accuracy.

I claim:

1. A mercury sphygmomanometer having a mercury passage in which a mercury column rises and falls according to the level of pressure, a mercury reservoir connected to said mercury passage, a calibration plate for reading the top of the mercury column in said mercury passage, a bulb and a cuff which are connected to said mercury reservoir through a tube, and a valve for opening and closing a communicating tube provided in between said mercury passage and said mercury reservoir in response to an operation of housing said constituent elements in a casing, wherein the improvement comprises:

an air pump connected to the top of said mercury passage through a tube; and a lever means for opening and closing said valve provided on said communicating tube, said air pump and said lever means being activated in harmony with each other in response to an operation of opening and closing a cover and such that said valve is closed after the mercury is evacuated into said mercury reservoir.

2. A mercury sphygmomanometer according to claim 1, wherein said air pump comprises: a cylinder having an air vent bored in the side wall thereof, and a rod constantly biased by means of a spring so as to retain a piston at the bottom dead center inside said cylinder.

3. A mercury sphygmomanometer according to claim 1, wherein said lever means for opening and closing said valve is arranged to come into contact with a first lever abutment provided upright on the bottom plate of said casing and a second lever abutment projecting from the side wall of said casing so that said lever means is pivotal through an angle of 90°.

* * * * *